US00PP35102P2

(12) United States Plant Patent
Miyazaki

(10) Patent No.: US PP35,102 P2
(45) Date of Patent: Apr. 11, 2023

(54) ***PETUNIA* PLANT NAMED 'SURF OHAKUNI'**

(50) Latin Name: ***Petunia* x *hybrida***
Varietal Denomination: Surf Ohakuni

(71) Applicant: Kiyoshi Miyazaki, Shiga (JP)

(72) Inventor: Kiyoshi Miyazaki, Shiga (JP)

(73) Assignee: SUNTORY FLOWERS LIMITED, Tokyo (JP)

( * ) Notice: Subject to any disclaimer, the term of this patent is extended or adjusted under 35 U.S.C. 154(b) by 0 days.

(21) Appl. No.: 17/844,349

(22) Filed: Jun. 20, 2022

(51) Int. Cl.
*A01H 5/02* (2018.01)
*A01H 6/82* (2018.01)

(52) U.S. Cl.
USPC ..... Plt./356.18
CPC ..... *A01H 6/824* (2018.05)

(58) Field of Classification Search
USPC ..... Plt./356.18
CPC ..... A01H 5/02
See application file for complete search history.

(56) References Cited

PUBLICATIONS https://viewer.joomag.com/2022-liner-catalog/0458788001628597960?page=171; Jul. 14, 2022; 4 pages.*
https://davis-floral.com/wp-content/uploads/2022/02/02-08-22-Davis-Liner-AV.pdf: Feb. 8, 2022, 2 pages.*
https://suntoryflowers.com/wp-content/uploads/2022/03/2023-SuntoryCatalog.pdf; Jul. 14, 2022; 2 pages.*

* cited by examiner

*Primary Examiner* — Kent L Bell
(74) *Attorney, Agent, or Firm* — C. Anne Whealy

(57) ABSTRACT

A new and distinct cultivar of *Petunia* plant named 'Surf Ohakuni', characterized by its upright to trailing and mounding plant habit; vigorous growth habit; freely branching habit; freely flowering habit; long flowering period; medium-sized flowers that are dark purplish red in color with dark purple-colored venation; and good garden performance.

1 Drawing Sheet

Figure 1:
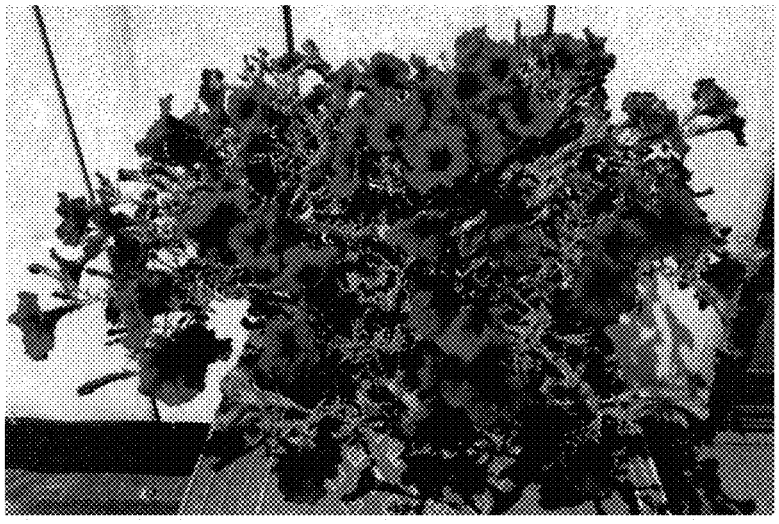

Botanical designation: *Petunia* x *hybrida*.
Cultivar denomination: 'SURF OHAKUNI'.

BACKGROUND OF THE INVENTION

The present invention relates to a new and distinct cultivar of *Petunia* plant, botanically known as *Petunia* x *hybrida* and hereinafter referred to by the name 'Surf Ohakuni'.

The new *Petunia* plant is a product of a planned breeding program conducted by the Inventor in Higashiomi, Shiga, Japan. The objective of the breeding program is to create new trailing and freely-branching habit *Petunia* plants with numerous large attractive flowers.

The new *Petunia* plant originated from a cross-pollination made by the Inventor in June, 2014 in Higashiomi, Shiga, Japan of a proprietary selection of *Petunia* x *hybrida* identified as code designation Px7109-04, not patented, as the female, or seed, parent with a proprietary selection of *Petunia* x *hybrida* identified as code designation K0272, not patented, as the male, or pollen, parent. The new *Petunia* plant was discovered and selected by the Inventor as a single flowering plant within the progeny of the stated cross-pollination in a controlled greenhouse environment in Higashiomi, Shiga, Japan in June, 2015.

Asexual reproduction of the new *Petunia* plant by terminal vegetative cuttings in a controlled greenhouse environment in Higashiomi, Shiga, Japan since April, 2016 has shown that the unique features of this new *Petunia* plant are stable and reproduced true to type in successive generations.

SUMMARY OF THE INVENTION

Plants of the new *Petunia* have not been observed under all possible combinations of environmental conditions and cultural conditions. The phenotype may vary somewhat with variations in environmental conditions such as temperature and light intensity without, however, any variance in genotype.

The following traits have been repeatedly observed and are determined to be the unique characteristics of 'Surf Ohakuni'. These characteristics in combination distinguish 'Surf Ohakuni' as a new and distinct *Petunia* plant:

1. Upright to trailing and mounding plant habit.
2. Vigorous growth habit.
3. Freely branching habit.
4. Freely flowering habit.
5. Long flowering period.
6. Medium-sized flowers that are dark purplish red in color with dark purple-colored venation.
7. Good garden performance.

Plants of the new *Petunia* can be compared to plants of the female parent selection. Plants of the new *Petunia* differ primarily from plants of the female parent selection in flower color as flowers of plants of the new *Petunia* are dark purplish red in color whereas flowers of plants of the female parent selection are red in color.

Plants of the new *Petunia* can be compared to plants of the male parent selection. Plants of the new *Petunia* differ primarily from plants of the male parent selection in plant size as plants of the new *Petunia* are broader than plants of the male parent selection.

Plants of the new *Petunia* can also be compared to plants of the *Petunia* x *hybrida* 'Surf Gorehana', disclosed in U.S.

Plant Pat. No. 29,691. In side-by-side comparisons, plants of the new *Petunia* and 'Surf Gorehana' differ primarily in the following characteristics:

1. Plants of the new *Petunia* have shorter internodes and more leaves per lateral branch than plants of 'Surf Gorehana'.
2. Plants of the new *Petunia* are more freely flowering than plants of 'Surf Gorehana'.
3. Plants of the new *Petunia* and 'Surf Gorehana' differ in flower color as flowers of plants of the new *Petunia* are dark purplish red in color whereas flowers of plants of 'Surf Gorehana' are bright red pink in color.
4. Petal venation of plants of the new *Petunia* is more distinct than petal venation of plants of 'Surf Gorehana'.
5. Sepals of plants of the new *Petunia* are shorter than sepals of plants of 'Surf Gorehana'.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the top of the sheet (FIG. 1) is a side perspective view of a typical flowering plant of 'Surf Ohakuni' grown in a container.

Figure 2:
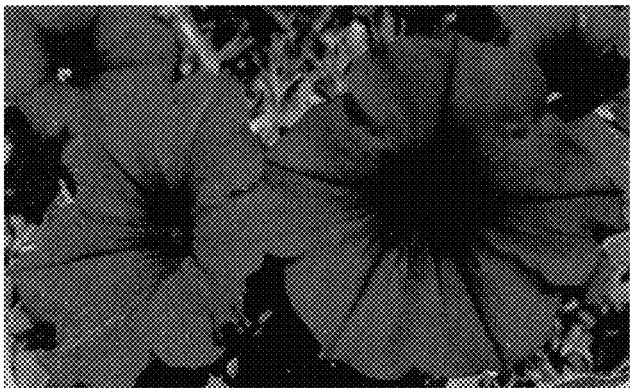

The photograph at the bottom of the sheet (FIG. 2) is a close-up view of typical flowers of 'Surf Ohakuni'.

DETAILED BOTANICAL DESCRIPTION

The aforementioned photographs and following observations, measurements and values describe plants grown during the early summer in 24-cm containers in an outdoor nursery in Higashiomi, Shiga, Japan and under cultural practices typical of commercial *Petunia* production. During the production of the plants, day temperatures averaged 23° C. and night temperatures averaged 13° C. Plants were six months old when the photographs and description were taken. In the following description, color references are made to The Royal Horticultural Society Colour Chart, 2015 Edition, except where general terms of ordinary dictionary significance are used.

Botanical classification: *Petunia* x *hybrida* 'Surf Ohakuni'.

Parentage:

*Female, or seed, parent*.—Proprietary selection of *Petunia* x *hybrida* identified as code designation Px7109-04, not patented.

*Male, or pollen, parent*.—Proprietary selection of *Petunia* x *hybrida* identified as code designation K0272, not patented.

Propagation:

*Type*.—By terminal vegetative cuttings.

*Time to initiate roots, summer and winter*.—About one week at temperatures about 15° C. to 20° C.

*Time to produce a rooted young plant, summer and winter*.—About three weeks at temperatures about 15° C. to 20° C.

*Root description*.—Fibrous; typically white in color, actual color of the roots is dependent on substrate composition, water quality, fertilizer type and formulation, substrate temperature and physiological age of roots.

*Rooting habit*.—Freely branching; dense.

Plant description:

*Plant form and growth habit*.—Upright to trailing and mounding plant habit; freely branching habit with numerous lateral branches developing per plant; pinching enhances lateral branch development; vigorous growth habit.

*Plant height*.—About 19 cm.

*Plant diameter*.—About 71 cm.

Lateral branch description:

*Length*.—About 23.8 cm.

*Diameter*.—About 2.9 mm.

*Internode length*.—About 1.6 cm.

*Strength*.—Strong, flexible.

*Aspect*.—Upright to mostly outwardly to eventually trailing.

*Texture*.—Densely pubescent; rough; viscid.

*Color*.—Close to 144A.

Leaf description:

*Quantity and arrangement*.—About 16 leaves per lateral branch; alternate, simple.

*Length*.—About 4 cm.

*Width*.—About 2.6 cm.

*Shape*.—Elliptic.

*Apex*.—Acuminate.

*Base*.—Attenuate.

*Margin*.—Entire.

*Texture, upper and lower surfaces*.—Sparsely pubescent; viscid.

*Venation pattern*.—Pinnate; reticulate.

*Color*.—Developing leaves, upper surface: Close to 137A. Developing leaves, lower surface: Close to 138A. Fully expanded leaves, upper surface: Close to 137B; venation, close to 138B. Fully expanded leaves, lower surface: Close to 138B; venation, close to 138C.

*Petioles*.—Length: About 3 mm. Diameter: About 3.2 mm. Texture, upper and lower surfaces: Pubescent; viscid. Color, upper and lower surfaces: Close to 138B.

Flower description:

*Flower arrangement and habit*.—Medium-sized single-type salverform flowers arising from upper leaf axils; freely flowering habit with usually about four flowers developing per lateral branch and about 209 flower buds and flowers developing per plant during the flowering season; flowers face mostly upright to outwardly.

*Fragrance*.—None detected.

*Natural flowering season*.—Early flowering habit; plants of the new *Petunia* initiate and develop flowers about three to four weeks after planting; long flowering period, flowering commences naturally during the spring and plants flower continuously throughout the summer until late autumn in Japan.

*Flower longevity*.—Individual flowers last about seven to ten days on the plant; flowers not persistent.

*Flower buds*.—Length: About 4.75 cm. Diameter: About 1.2 mm. Shape: Cylindrical. Color: Immature sepals, close to N187A; immature petals, close to N186A.

*Flower diameter*.—About 5.8 cm.

*Flower tube length*.—About 3.2 cm.

*Flower tube diameter, proximally*.—About 3.8 mm.

*Flower tube diameter, distally*.—About 1.25 cm.

*Corolla*.—Quantity and arrangement: Five in a single whorl, fused at the base and opening into a flared trumpet. Petal length from throat: About 2.1 cm. Petal width: About 2.8 cm. Petal shape: Roughly spatulate. Petal apex: Cuspidate. Petal margin: Entire; slightly undulate. Petal texture, upper and lower surfaces: Smooth, glabrous; velvety. Throat texture: Smooth, glabrous; velvety. Tube texture: Pubescent, rough. Color: Petal, when opening, upper surface: Close to N79A. Petal, when opening, lower surface: Close to N81A. Petal, fully opened, upper surface: Close to N79C; venation, close to N187A; color becoming closer to 72A with subsequent development. Petal, fully opened, lower surface: Close to 72A; venation, close to 72A; color does not change with subsequent development. Throat: Distally, close to N186A; mid-section, close to 203C; proximally, close to 203C and N77B; venation, close to 187A. Tube: Distally, close to N92C; proximally, close to N77A; venation, similar to lamina colors.

*Calyx*.—Arrangement: One star-shaped calyx tube with five sepals arranged in a single whorl and fused at the base. Sepal length: About 1 cm. Sepal width: About 3.4 mm. Sepal shape: Linear. Sepal apex: Acute. Sepal margin: Entire. Sepal texture, upper and lower surfaces: Densely pubescent; viscid. Color, upper surface: Close to 138A. Color, lower surface: Close to 137C.

*Peduncles*.—Length: About 1.4 cm. Diameter: About 1.6 mm. Strength: Moderately strong, flexible. Aspect: Upright to outwardly. Texture: Densely pubescent; viscid. Color: Close to NN137B.

*Reproductive organs*.—Stamens: Quantity per flower: Five. Filament length: About 1.3 cm. Filament color: Close to 145C and 72B. Anther shape: Ellipsoidal. Anther size: About 2.5 mm by 3 mm. Anther color: Close to 91D. Pollen amount: Moderate. Pollen color: Close to 92B. Pistils: Quantity per flower: One. Pistil length: About 2.3 cm. Style color: Close to 145C. Stigma shape: Transversely ellipsoidal. Stigma color: Close to 145A. Ovary color: Close to 142A. Seeds and fruits: To date, seed and fruit development have not been observed on plants of the new *Petunia*.

Garden performance: Plants of the new *Petunia* have been observed to have good garden performance and to tolerate rain, wind and temperatures ranging from about 5° C. to about 35° C.

Pathogen & pest resistance: To date, plants of the new *Petunia* have not been observed to be resistant to pathogens and pests common to *Petunia* plants.

It is claimed:

1. A new and distinct *Petunia* plant named 'Surf Ohakuni' as illustrated and described.

* * * * *